United States Patent [19]

Alpegiani et al.

[11] Patent Number: 5,587,373
[45] Date of Patent: Dec. 24, 1996

[54] 2-ACYLOXYCEPHEM DERIVATIVES

[75] Inventors: Marco Alpegiani, Milan; Pierluigi Bissolino, San Giorgio di Lomellina; Ettore Perrone, Boffalora Ticino, all of Italy

[73] Assignee: Farmitalia Carlo Erba S.r.l., Milan, Italy

[21] Appl. No.: 331,483

[22] PCT Filed: Feb. 24, 1994

[86] PCT No.: PCT/EP94/00529

§ 371 Date: Nov. 4, 1994

§ 102(e) Date: Nov. 4, 1994

[87] PCT Pub. No.: WO94/20504

PCT Pub. Date: Sep. 15, 1994

[30] Foreign Application Priority Data

Mar. 4, 1993 [GB] United Kingdom ............... 9304440

[51] Int. Cl.⁶ .................. C07D 501/04; C07D 501/14; C07D 501/60; A61K 31/545
[52] U.S. Cl. .................. 514/202; 514/204; 514/207; 504/230; 504/122.3; 504/226
[58] Field of Search .................. 540/230, 223, 540/226; 514/207, 202, 204

[56] References Cited

U.S. PATENT DOCUMENTS 5,077,286  12/1991  Bissolino et al. .................. 514/201
5,348,952   9/1994  Bissolino et al. .................. 514/202

*Primary Examiner*—Cecilia Tsang
*Assistant Examiner*—King Lit Wong
*Attorney, Agent, or Firm*—Oblon, Spivak, McClelland, Maier & Neustadt, P.C.

[57] ABSTRACT

The present invention provides cephalosporin sulphones of formula (I) and the pharmaceutically and veterinarily acceptable salts thereof:

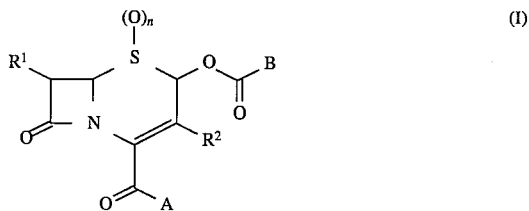

wherein n is one or two:

A and B are both or each independently hydrogen or an organic radical;

$R^1$ represents halogen, A, OA, —S(O)$_m$A wherein m is 0–2, —OC(O)A, —OS(O)$_2$A, —NHC(O)A or —NH—Z wherein Z is a mono, di- or tripeptide and A is as defined above;

$R^2$ represents a halogen, A, —S(O)$_m$A, —O—A, —C(O)A, —C(O)OA, —CH$_2$—OA, —CH$_2$S(O)$_m$A, —CH$_2$OC(O)A, —CH$_2$O—Z, —CH$_2$SC(O) A, —CH$_2$—N(A)A, —CH$_2$N$^+$(A)(A')A", —CH$_2$NH—C(O)A or —CH$_2$NH—Z wherein A and Z are as defined above.

The compounds of formula (I) and their salts are elastase inhibitors.

12 Claims, No Drawings

2-ACYLOXYCEPHEM DERIVATIVES

The present invention relates to new cephalosporins, their preparation and to pharmaceutical and veterinary compositions containing them.

The compounds disclosed in the present invention are cephem sulphones or sulphoxides featuring the simultaneous presence on the cephem skeleton of an acyl group at C-4 and an acyloxy group at C-2.

According to the invention there are provided cephalosporin sulphones of formula (I) and the pharmaceutically and veterinarily acceptable salts thereof:

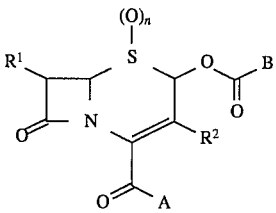

(I)

wherein n is one or two:

A and B are each, independently, hydrogen or an organic radical selected from optionally substituted $C_1$–$C_{12}$ straight or branched alkyl, $C_2$–$C_{12}$ alkenyl, $C_2$–$C_{12}$ alkynyl, $C_6$–$C_{14}$ aryl, $C_3$–$C_8$ cycloalkyl, $C_5$–$C_8$ cycloalkenyl, or $C_7$–$C_{18}$ aralkyl, $C_8$–$C_{18}$ aralkenyl, $C_8$–$C_{18}$ aralkynyl, (cycloalkyl)alkyl, (cycloalkyl)alkenyl, heterocyclyl, (heterocyclyl)alkyl and (heterocyclyl)alkenyl groups;

$R^1$ represents
(1) a chlorine, fluorine, bromine or iodine atom
(2) A as defined above
(3) an ether OA wherein A is as defined above
(4) a thioether, sulphoxide or sulphone —S(O)$_m$A wherein m is either zero, one or two and A is as defined above;
(5) acyloxy —OC(O)A wherein A is as defined above;
(6) sulphonyloxy —OS(O)$_2$A wherein A is as defined above;
(7) an acylamino group —NHC(O)A wherein A is as defined above or acylamino —NH—Z wherein Z is a mono, di- or tripeptide composed of D or L α-aminoacids chosen from Ala, Gly, Val, Leu, Ile and Phe, and in which α-amino acids the terminal amino group is either free or acylated by a group —C(O)A or —C(O)OA wherein A is as defined above;

$R^2$ represents:
(1) A as defined above;
(2) a chlorine or fluorine atom;
(3) a sulphenyl, sulphinyl or sulfonyl group —S(O)$_m$A wherein A is as defined above;
(4) an oxy group —O—A wherein A is as defined above;
(5) an acyl group —C(O)A or acyloxy group —C(O)OA wherein A is as defined above;
(6) an oxymethyl group —CH$_2$—OA wherein A is as defined above;
(7) a thiomethyl group or a derivative thereof of formula —CH$_2$S(O)$_m$A wherein m and A are as defined above;
(8) an acyloxymethyl group —CH$_2$OC(O)A or —CH$_2$O—Z wherein A and Z are as defined above;
(9) an acylthiomethyl group —CH$_2$SC(O)A wherein A is as defined above;
(10) an aminomethyl group —CH$_2$—N(A)A' wherein A is as defined above and A', being the same or different, is as defined above for A; or A and A' taken together with the nitrogen atom to which they are attached represent a heterocyclic ring;
(11) ammoniomethyl —CH$_2$N$^+$(A)(A')A" wherein A and A' are as defined above and A", being the same or different, is as defined for A; or A is alkyl and A' and A" together with the nitrogen atom to which they are attached represent a heterocyclic ring, or A and A' and A" together with the nitrogen atom to which they are attached represent a heterocyclic ring;
(12) an acylaminomethyl group —CH$_2$NH—C(O) A or —CH$_2$NH—Z wherein A and Z are as defined above.

As referred to herein a $C_1$–$C_{12}$ alkyl group is straight or branched, for instance $C_1$–$C_{10}$ alkyl, typically $C_1$–$C_6$ alkyl or $C_1$–$C_4$ alkyl. Examples include methyl, ethyl, n-propyl, isopropyl, n-butyl, isobutyl, sec-butyl, tert-butyl, n-pentyl, n-hexyl and so on.

A $C_2$–$C_{12}$ alkenyl group is straight or branched, for instance $C_2$–$C_{10}$ alkenyl, typically $C_2$–$C_6$ alkenyl or $C_2$–$C_4$ alkenyl. Examples include vinyl, allyl, crotyl, 2-methyl-1-propenyl, 1-methyl-1-propenyl, butenyl, pentenyl and so on.

A $C_2$–$C_{12}$ alkynyl group is straight or branched, for instance $C_2$–$C_{10}$ alkynyl, typically $C_2$–$C_6$ alkynyl or $C_2$–$C_4$ alkynyl. Examples include ethynyl, propargyl, 1-propynyl, 1-butynyl, 2-butynyl and so on.

A $C_6$–$C_{14}$ aryl group is preferably a monocyclic, bicyclic or tricyclic aromatic hydrocarbon group of 6 to 14 carbon atoms, such as phenyl, naphthyl, phenanthryl or anthryl.

A $C_3$–$C_8$ cycloalkyl group is preferably a saturated carbocyclic group of 3 to 6 carbon atoms, such as cyclopropyl, cyclobutyl, cyclopentyl, cyclohexyl and so on.

A $C_5$–$C_8$ cycloalkenyl group is preferably an unsaturated carbocyclic group such as cyclopentenyl, cyclohexenyl and so on.

A $C_7$–$C_{18}$ aralkyl group is preferably an alkyl group of 1 to 4 carbon atoms linked to a monocyclic, bicyclic or tricyclic aromatic hydrocarbon group of 6 to 14 carbon atoms. Examples of aralkyl groups are benzyl, phenylethyl, naphthylmethyl, naphthylethyl and anthrylmethyl.

A $C_8$–$C_{18}$ aralkenyl group is preferably an alkenyl group of 2 to 4 carbon atoms linked to a monocyclic, bicyclic or tricyclic aromatic hydrocarbon group of 6 to 14 carbon atoms. Examples of aralkenyl groups are styryl, 2-phenyl-1-propenyl, 3-phenyl-2-butenyl, 2-naphthylethenyl, anthrylethenyl and so on.

A $C_8$–$C_{14}$ aralkynyl group is preferably an alkynyl group of 2 to 4 carbon atoms linked to a monocyclic, bicyclic or tricyclic aromatic hydrocarbon group of 6 to 10 carbon atoms. Examples of aralkynyl groups are 2-phenylethynyl, 2-naphthylethynyl, anthrylethynyl and so on.

A (cycloalkyl)alkyl group is preferably an alkyl group of 1 to 4 carbon atoms linked to a cycloalkyl group.

A (cycloalkyl)alkenyl group is preferably an alkenyl group of 2 to 4 carbon atoms linked to a cycloalkyl group or to an aryl group.

A heterocyclyl group is preferably a 3- to 6-membered, saturated or unsaturated heterocyclyl ring, containing at least one heteroatom selected from O, S and N, which is optionally fused to a second 5- or 6-membered, saturated or unsaturated heterocyclyl group or to a cycloalkyl group or to an aryl group.

A (heterocyclyl)alkyl group is preferably an alkyl group of 1 to 4 carbon atoms linked to a heterocyclyl group.

A (heterocyclyl)alkenyl group is preferably an alkenyl group of 2 to 4 carbon atoms linked to a heterocyclic group.

The term halogen or halo preferably denotes fluorine, chlorine or bromine.

The above said alkyl, alkenyl, alkynyl, cycloalkyl, cycloalkenyl, aryl, aralkyl, aralkenyl, aralkynyl, (cycloalkyl)alkyl, (cycloalkyl)alkenyl, heterocyclyl, (heterocyclyl)alkyl and (heterocyclyl)alkenyl groups can be either unsubstituted or substituted by one or more substituents selected from:

halo (e.g., fluoro, bromo, chloro or iodo);

hydroxy;

nitro;

azido;

mercapto (—SH);

amino (i.e., —NH$_2$, or —NHR$^i$ or —NR$^i$R$^{ii}$) wherein R$^i$ and R$^{ii}$, which are the same or different, are C$_1$–C$_{12}$ straight or branched alkyl or phenyl or benzyl; or phenyl optionally substituted by one or more halogen atoms or carboxy groups;

formyl (i.e., —CHO);

cyano;

carboxy(alkyl) (i.e., (CH$_2$)$_t$COOH or (CH$_2$)$_t$COOR$^i$) wherein R$^i$ is as defined above and t is 0, 1, 2 or 3;

sulfo (i.e., —SO$_3$H);

acyl (i.e., —C(O)R$^i$) wherein R$^i$ is as defined above or trifluoroacetyl (i.e., —C(O)CF$_3$);

carbamoyl (i.e., —CONH$_2$); N-methylcarbamoyl (i.e., —CONHCH$_3$) or N-carboxymethylcarbamoyl (i.e., —CONHCH$_2$COOH);

carbamoyloxy (i.e., —OCONH$_2$);

acyloxy (i.e., —OC(O)R$^i$) wherein R$^i$ is as defined above or formyloxy (i.e., —OC(O)H);

alkoxycarbonyl or benzyloxycarbonyl (i.e., —C(O)OR$^i$) wherein R$^i$ is as defined above;

alkoxycarbonyloxy or benzyloxycarbonyloxy (i.e., —OC(O)OR$^i$) wherein R$^i$ is as defined above;

alkoxy, phenoxy or benzyloxy (i.e., —OR$^i$) wherein R$^i$ is as defined above;

alkylthio, phenylthio or benzylthio (i.e., —SR$^i$) wherein R$^i$ is as defined above;

alkylsulfinyl, phenylsulfinyl or benzylsulfinyl (i.e., —S(O)R$^i$) wherein R$^i$ is as defined above;

alkylsulfonyl, phenylsulfonyl or benzylsulfonyl (i.e., —S(O)$_2$R$^i$) wherein R$^i$ is as defined above;

acylamino (i.e., —NHC(O)R$^{iii}$ or —NHC(O)OR$^{iii}$) wherein R$^{iii}$ is C$_1$–C$_{12}$ straight or branched alkyl, phenyl, benzyl, CH$_2$CH$_2$COOH or CH$_2$CH$_2$CH$_2$COOH;

sulfonamido (i.e., —NHSO$_2$R$^i$) wherein R$^i$ is as defined above;

guanidino (i.e., —NHC(=NH)NH$_2$);

C$_1$–C$_4$ alkyl, C$_2$–C$_4$ alkenyl or alkynyl;

C$_3$–C$_6$ cycloalkyl;

substituted methyl selected from chloromethyl, fluoromethyl, difluoromethyl, trifluoromethyl, aminomethyl, N,N-dimethylaminomethyl, azidomethyl, cyanomethyl, carboxymethyl, sulfomethyl, carbamoylmethyl, carbamoyloxymethyl, hydroxymethyl, C$_1$–C$_4$ alkyloxycarbonylmethyl, guanidinomethyl.

phthalimido, indolyl, indolinyl, isoindolinyl, 1-oxoisoindolinyl.

The heterocyclic group may in particular be chosen from:

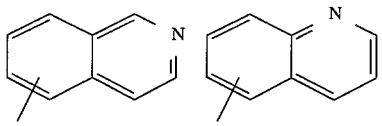

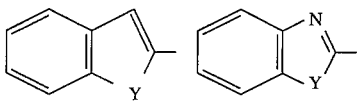

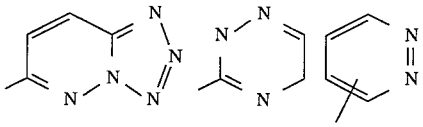

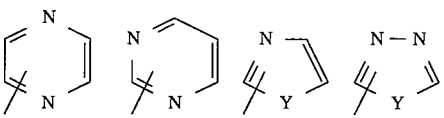

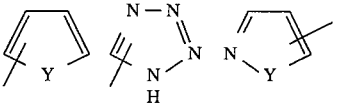

wherein Y is S, O or NH

Any of the above heterocyclic groups may be totally or partially reduced.

More preferably, the heterocyclic group is chosen from:

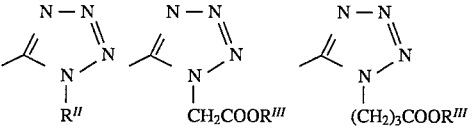

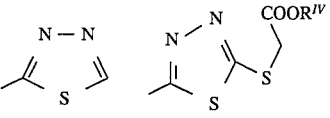

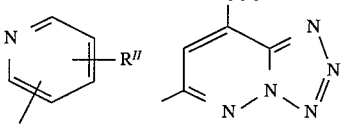

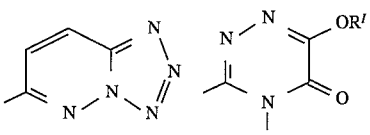

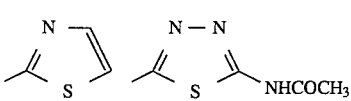

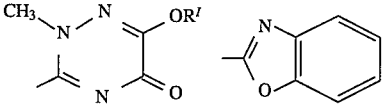

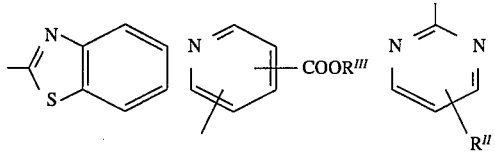

wherein R' is, typically, hydrogen, methyl, allyl or benzyl, or a hydroxy protecting group; R'' is hydrogen, methyl, ethyl, propyl, phenyl, benzyl, carboxymethyl, 2-carboxyethyl, 3-carboxypropyl, 3-benzhydryloxycarbonylpropyl, sulphoethyl, 2,2-dimethylaminoethyl and R''' is typically hydrogen, methyl, allyl or benzyl or a carboxy protecting group.

The carboxy-protecting group may, for example, be a lower alkyl group such as methyl, ethyl, propyl, isopropyl or tert-butyl; a halogenated lower alkyl group such as 2,2,2-trichoroethyl or 2,2,2-trifluoroethyl; a lower alkanoyloxyalkyl group such as acetoxymethyl, propionyloxymethyl, pivaloyloxymethyl, 1-acetoxyethyl, 1-propionyloxyethyl; a lower alkoxycarbonyloxyalkyl group such as 1-(methoxycarbonyloxy)ethyl, 1-(ethoxycarbonyloxy) ethyl, 1-(isopropoxycarbonyloxy)ethyl; a lower alkenyl group such as 2-propenyl, 2-chloro-2-propenyl, 3-methoxycarbonyl-2-propenyl, 2-methyl-2-propenyl, 2-butenyl, cinnamyl; an aralkyl group such as benzyl, p-methoxybenzyl, 3,4-dimethoxybenzyl, o-nitrobenzyl, p-nitrobenzyl, benzhydryl, bis(p-methoxyphenyl)methyl; a (5-substituted 2-oxo-1,3-dioxol-4-yl)methyl group such as (5-methyl-2-oxo-1,3-dioxol-4-yl)methyl; a lower alkylsilyl group such as trimethylsilyl, tert-butyldimethylsilyl, tert-butyldiphenylsilyl, triphenylsilyl; or an indanyl group; a phthalidyl group; a pyranyl group; a methoxymethyl or methylthiomethyl group; a 2-methoxyethoxymethyl group. Particularly preferred are a tert-butyl group, a p-nitrobenzyl group, a p-methoxybenzyl group, a benzhydryl group, a tert-butyldimethylsilyl, tert-butyldiphenylsilyl group or a propenyl group.

The amino, hydroxy or mercapto protecting groups which may optionally be present are any of those usually employed in the chemistry of penicillins and cephalosporins for this kind of function. They may be, for instance, optionally substituted, especially halo-substituted, acyl groups, e.g. acetyl, monochloroacetyl, dichloroacetyl, trifluoroacetyl, benzoyl or p-bromophenacyl; triarylmethyl groups, e.g. triphenylmethyl; silyl groups, in particular trimethylsilyl, dimethyl-tert-butylsilyl, diphenyl-tert-butylsilyl,; or also groups such as tert-butoxycarbonyl, p-nitrobenzyloxycarbonyl, 2,2,2-trichloroethoxycarbonyl, benzyl and pyranyl. Preferred protecting groups of the hydroxy function are p-nitrobenzyloxycarbonyl; allyloxycarbonyl; dimethyl-tert-butylsilyl; diphenyl-tert-butylsilyl; trimethylsilyl; 2,2,2-trichloroethoxycarbonyl; benzyl; dimethoxybenzyl; p-methoxybenzyloxycarbonyl; p-bromophenacyl; triphenylmethyl, pyranyl, methoxymethyl, benzhydryl, 2-methoxyethoxymethyl, formyl, acetyl, trichloroacetyl.

The present invention provides the salts of those compounds of formula (I) that have salt-forming groups, especially the salts of the compounds having a carboxylic group, a basic group (e.g. an amino or guanidino group), or a quaternary ammonium group. The salts are pharmaceutically or veterinarily acceptable salts, for example alkali metal and alkaline earth metal salts (e.g. sodium, potassium, lithium, calcium and magnesium salts), ammonium salts and salts with an appropriate organic amine or amino acid (e.g. arginine, procaine salts), and the addition salts formed with suitable organic or inorganic acids, for example hydrochloric acid, sulphuric acid, carboxylic and sulphonic organic acids (e.g. acetic, trifluoroacetic, p-toluensulphonic acid). Some compounds of formula (I) which contain a carboxylate and an ammonium group may exist as zwitterions; such salts are also part of the present invention.

Furthermore, physiologically hydrolyzable esters, hydrates and solvates of compounds of formula (I) are included within the scope of the present invention. The physiologically hydrolyzable esters of the compounds (I) may include, for example, methoxycarbonylmethyl, 1-methoxycarbonyloxy-1-ethyl, indanyl, phthalidyl, methoxymethyl, pivaloyloxymethyl, glycyloxymethyl, phenylglycyloxymethyl or 5-methyl-2-oxo-1,3-dioxolan-4-yl esters, and other physiologically hydrolyzable esters which have been widely used in the technical fields of penicillin and cephalosporin antibiotics: more preferably, methoxycarbonyloxymethyl, 1-methoxycarbonyloxy,1-ethyl, methoxymethyl or pivaloyloxymethyl; and most preferably, methoxycarbonyloxymethyl or methoxymethyl. Typical solvates of the cephalosporin compounds of formula(I) may include solvates with water miscible solvents, e.g. methanol, ethanol, acetone; or acetonitrile; and more preferably, ethanol.

The present invention also provides a pharmaceutical composition comprising, as an active principle, a compound of formula (I) or salt thereof, in association with one or more pharmaceutically acceptable carriers, excipients or other additives, if necessary.

The present invention encompasses all the possible stereoisomers of compounds of formula (I) as well as their racemic or optically active mixtures. However the configuration depicted in formula (1') is particularly preferred

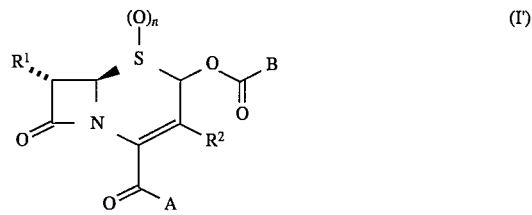

wherein n is one or two;

A is hydrogen or $C_1$–$C_{12}$ straight or branched alkyl, $C_2$–$C_{12}$ alkenyl, $C_2$–$C_{12}$ alkynyl, $C_6$–$C_{10}$ aryl, $C_3$–$C_8$ cycloalkyl, heterocyclyl, 2-phenyl-2-propyl, benzyl or diphenylmethyl, wherein the alkyl, alkenyl, alkynyl, aryl, cycloalkyl, heterocyclyl and benzyl groups are either unsubstituted or substituted by fluoro, chloro, sulfo, carboxy, $C_1$–$C_4$ alkoxy, $C_1$–$C_4$ alkoxycarbonyl, carbamoyl, sulfamoyl, carbamoyloxy, methanesulphonyl, nitro, cyano, diazo, hydroxy, methoxy, ethoxy, tert-butoxy, benzyloxy, benzhydryloxy, acetoxy, pivaloyloxy, benzoxy, carboxymethyl, carboxyphenyl $C_6H_5$—COOH, carboxybenzyl $CH_2$—$C_6H_4$—COOH, benzoyl, pivaloyl, amino, formamido, acetamido, trifluoroacetamido or pivalamido;

B is
(1') a hydrogen atom;
(2') an optionally substituted $C_1$–$C_5$ straight or branched alkyl or alkenyl group or $C_3$–$C_6$ cycloalkyl;
(3') optionally substituted $C_6$–$C_{14}$ aryl;
(4') optionally substituted $C_7$–$C_{15}$ aralkyl;
(5') optionally substituted heterocyclyl;
(6') optionally substituted (heterocyclyl)alkyl;
the substituents for the groups defined under (1')–(6') being selected from fluoro, chloro, bromo, nitro, cyano, sulfo, carboxy, tetrazolyl, $C_1$–$C_4$ alkoxycarbonyl, carbamoyl,N- carboxyphenylcarbamoyl, N-carboxybenzylcarbamoyl, N-carboxymethylphenylcarbamoyl, sulfamoyl, carbamoyloxy, methanesulfonyl, hydroxy, $C_1$-$C_4$ alkoxy, benzyloxy, benzhydryloxy, phenoxy, p-chlorophenoxy, p-carboxyphenoxy, acetoxy, pivaloyloxy, benzoyloxy, methylthio, phenylthio, methanesulfonyl, benzenesulfonyl, carboxymethylthio, carboxyphenyl $C_6H_5$—COOH, carboxybenzyl $CH_2$—$C_6H_5$—COOH, acetyl, trifluoroacetyl, benzoyl, pivaloyl, amino, dimethylamino, phenylamino, 2,6-dichlorophenylamino diethylamino, formamido, acetamido, trifluoroacetamido, pivalamido, oxo, phenyl, phthalimido, isoindolinyl, 1-oxoisoindolinyl and $C_1$-$C_5$ straight or branched alkyl, vinyl or allyl, and $C_1$-$C_4$ alkyl substituted by one or more substituents selected from chloro, fluoro, difluoro, trifluoro, amino, N,N dimethylamino, azido, cyano, carboxy, sulfo, carbamoyl, carbamoyloxy, hydroxy, $C_1$-$C_4$ alkyloxycarbonyl, guanidino and a group Y-A''', wherein Y is oxygen, sulphur or carbamoyl(oxy) and A''' is an optionally substituted $C_1$-$C_4$ alkyl, phenyl, benzyl or heterocyclic group, the optional substituents being selected from those defined above for groups (1')-(5');

$R^1$ is
  (1') hydrogen or a chlorine, fluorine or bromine atom
  (2') $C_1$-$C_4$ alkyl, $C_1$-$C_4$ alkenyl, 1-(hydroxy)ethyl, 1-(benzyloxy)ethyl, 1-(benzyloxycarbonyloxy)ethyl, 1-(phenylacetoxy)ethyl, 2-fluoro-1-hydroxyethyl, phenyl or benzyl
  (3') methoxy, ethoxy, isopropoxy, phenoxy or benzyloxy
  (4') methylthio, ethylthio, isopropylthio
  (5') formyloxy, acetoxy or phenylacetoxy
  (6') mesyloxy or tosyloxy
  (7') formamido, acetamido, fluoroacetamido, trifluoroacetamido or chloroacetamido
  (8') $R^{iv}$-Ala-NH, wherein $R^{iv}$ is acetyl, tert-butoxycarbonyl, benzoxycarbonyl or HOOC—$CH_2CH_2C(O)$—;
  (9') $R^{iv}$-Val-NH, wherein $R^{iv}$ is as defined above;
  (10') Val-Pro-NH, LysNH or Ala-Ala-ProNH, wherein the terminal amino group of Val, Lys or Ala respectively or the α-amino group of Lys is either free or acylated with a group $R^{iv}$ as defined above;

$R^2$ is either hydrogen or
  (1') methyl, chloromethyl, bromomethyl, benzyl, ethyl, propyl or phenyl
  (2') chloro
  (3') methoxy or benzyloxy
  (4') methylthio
  (5') formyl, acetyl, benzoyl, carboxy, methoxycarbonyl, ethoxycarbonyl, tert-butoxycarbonyl or benzyloxycarbonyl;
  (6') methoxymethyl, ethoxymethyl, isopropoxymethyl; or benzyloxymethyl, phenoxymethyl, 3-pyridyloxymethyl wherein the phenyl and pyridyl rings are either unsubstituted or substituted by one group or two groups which are the same or different and are each chosen from hydroxy, carboxy, amino and $C_1$-$C_4$ alkoxycarbonyl;
  (7') —$CH_2(S)_n$A wherein n is zero, one or two and A is as defined above;
  (8') acetoxymethyl, benzoyloxymethyl, phenylacetoxymethyl or $C_3$-$C_6$ alkanoyloxymethyl, which groups are either unsubstituted or substituted by one or more groups selected from carboxy, hydroxy and $C_1$-$C_3$ alkoxy;
  (9') trialkylammoniomethyl wherein the alkyl group is methyl, ethyl or propyl; N-methylpyrrolidiniomethyl, N-methylpiperidimiomethyl or N-methylmorpholiniomethyl;
  (10') pyridiniomethyl which is either unsubstituted or substituted on the heterocyclic ring by fluoro, chloro, methoxy, hydroxy, carboxy or carbamoyl;
  (11') carbamoyloxymethyl; or
  (12') carboxy;

and the pharmaceutically and veterinarily acceptable salts thereof and all the possible isomers, e.g. stereoisomers, epimers, diastereoisomers, geometrical isomers, tautomers.

Still more preferred are compounds of formula (I') wherein n is two;

A is selected from tert-butyl, phenyl, 1-phenylethyl, 2-phenyl-2-propyl, 4-benzylphenyl, biphenylyl, naphthyl and tolyl, any of which is optionally substituted by a $C_1$-$C_4$ alkyl group or a carboxy group;

B is
  (1") methyl, ethyl, vinyl, propyl, allyl, isopropyl, n-butyl, s-butyl, tert-butyl, pentyl, optionally substituted by a group selected from carboxy, sulfo, amino, cyano, methoxy, phenoxy, naphthyloxy, p-chlorophenoxy, p-carboxyphenoxy;
  (2") a phenyl group optionally substituted by one or two groups selected from fluoro, chloro, bromo, iodo, $C_1$-$C_5$ alkyl, methoxy, methylthio, methanesulfonyl, carboxy, tert-butoxycarbonyl, benzhydryloxycarbonyl, carboxymethyl, sulfo, sulfomethyl, carboxymethylthio, carboxymethoxy, nitro, cyano, amino, dimethylamino, phenylamino, 2,3 dimethylphenylamino, dibutylamino, hydroxy, acetamido, trifluorocetamido, acetyl, trifluoroacetyl, carbamoyl and sulfamoyl;
  (3") naphthyl, optionally substituted by one or two groups selected from fluoro, chloro, bromo, iodo, $C_1$-$C_4$ alkyl, methoxy, methylthio, methanesulfonyl, carboxy, tert-butoxycarbonyl, benzhydryloxycarbonyl, carboxymethyl, carboxymethylthio, carboxymethoxy, sulfo, sulfomethyl, nitro, cyano, amino, dimethylamino, hydroxy, acetamido, trifluorocetamido, acetyl, trifluoroacetyl, carbamoyl and sulfamoyl;
  (4") anthryl or phenanthryl, optionally substituted by one or two groups selected from fluoro, chloro, bromo, iodo, $C_1$-$C_4$ alkyl, methoxy, methylthio, methanesulfonyl, carboxy, tert-butoxycarbonyl, benzhydryloxycarbonyl, carboxymethyl, carboxymethylthio, carboxymethoxy, sulfo, sulfomethyl, nitro, cyano, amino, dimethylamino, hydroxy, acetamido, trifluorocetamido, acetyl, trifluoroacetyl, carbamoyl and sulfamoyl;
  (5") biphenyl —$C_6H_4$—$C_6H_5$, optionally substituted by a carboxy, sulfo, carboxymethyl or sulfomethyl group;
  (6") a heterocycle chosen from thiazole, tetrazole, thiadiazole, triazole, isothiazole, oxazole, isoxazole, pyridine, pyrimidine, pyridazine, quinoline, isoquinoline, benzothiazole, benzoxazole, furan, thiophene, pyrrole, indole, chromane, benzofuran and benzothiophene either unsubstituted or substituted by one or two groups selected from fluoro, chloro, bromo, iodo, straight or branched $C_1$-$C_4$ alkyl, methoxy, methylthio, methanesulfonyl, carboxy, tert-butoxycarbonyl, benzhydryloxycarbonyl, carboxymethyl, carboxymethylthio, carboxymethoxy, sulfo, sulfomethyl, nitro, cyano, amino, dimethylamino, dimethylaminoethyl, hydroxy, acetamido, trifluoroacetamido, acetyl, trifluoroacetyl, carbamoyl and sulfamoyl;

(7") phenyl substituted by t-butyl, N-carboxyphenylcarbamoyl, N-carboxybenzylcarbamoyl or N-carboxymethylphenylcarbamoyl or by methyl substituted by a group Y—A''', wherein Y is O, S or OCONH and A''' is tetrazole, thiadiazole, pyridine, triazole, $C_1$–$C_4$ alkyl, phenyl or benzyl either unsubstituted or substituted by one or two groups selected from $C_1$–$C_4$ alkyl, methansulfonyl, carboxy, sulfo, amino, hydroxy, oxo, acetamido, carboxymethyl and carboxymethylthio;

(8") phenyl($C_1$–$C_4$)alkyl or naphthyl($C_1$–$C_4$)alkyl, with yhe phenyl and naphthyl rings optionally substituted by $C_1$–$C_5$ alkyl, $C_1$–$C_4$ alkoxy, phenoxy, benzoyl, phenylamino, 2,6-dichlorophenylamino, phenyl, p-chlorophenyl, naphthyl, chloro, fluoro, hydroxy, carboxy, nitro, phthalimido, isoindolinyl, 1-oxoisoindolinyl.

$R^1$ is hydrogen or a chlorine, fluorine or bromine atom, or a methoxy, ethoxy, propoxy, isopropoxy, allyloxy, methylthio, ethylthio, isopropylthio, formamido, acetamido, trifluoroacetamido, chloroacetamido, methyl, ethyl, isopropyl, allyl or hydroxyethyl group;

$R^2$ is either hydrogen or methyl, chloromethyl, bromomethyl, methoxymethyl, carbamoyloxymethyl, carboxy, phenoxymethyl, 3-pyridyloxymethyl, acetoxymethyl, benzoyloxymethyl, p-carboxybenzoyloxymethyl, aminomethyl, pyridiniomethyl, glycyloxymethyl or a —$CH_2$—S—Het group wherein Het is a heterocyclic ring preferably chosen from

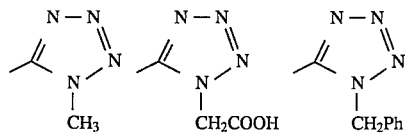

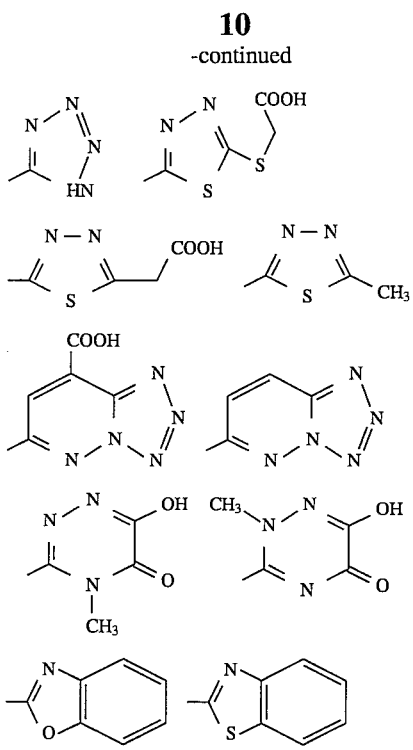

and the pharmaceutically and veterinarily acceptable salts thereof, and all the possible isomers including stereoisomers such as epimers, diastereoisomers, geometrical isomers, tautomers. Possible enolic forms of the above described compounds are to be considered tautomers of compounds of formula (I') and fall within the scope of the present invention.

Specific examples of the preferred compounds of the present invention are those listed in Table I.

TABLE 1

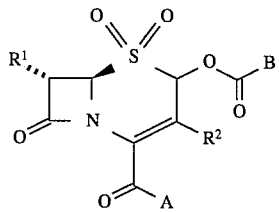

| n | $R^1$ | $R^2$ | A | B |
|---|-------|-------|---|---|
| 1 | Cl | $CH_3$ | t-Bu | Ph |
| 2 | $CH_3O$ | $CH_3$ | t-Bu | Ph |
| 3 | $CH_3O$ | $CH_3$ | t-Bu | —C$_6$H$_4$—CO$_2$H |
| 4 | $CH_3O$ | $CH_3$ | t-Bu | —C$_6$H$_4$—CH$_2$CO$_2$H |

TABLE 1-continued

| n | R¹ | R² | A | B |
|---|----|----|----|---|
| 5 | " | " | " | 3-carboxyphenyl |
| 6 | " | " | " | $CH_3$ |
| 7 | " | " | " | $CH_2Ph$ |
| 8 | " | " | " | $CH_2OPh$ |
| 9 | " | " | " | $CH_2CH_2CO_2H$ |
| 10 | " | " | " | $CH(OH)Ph$ |
| 11 | " | " | " | 2-naphthyl |
| 12 | " | " | " | $-CH_2-$C$_6$H$_4$-$CO_2H$ (para) |
| 13 | " | " | " | 2-pyridyl |
| 14 | " | " | " | $-CH_2$-pyridazin-3-yl |
| 15 | $CH_3O$ | $CH_3$ | t-Bu | $CH_2$-(2-amino-thiazol-4-yl) |
| 16 | $CH_3O$ | $CH_2OCOCH_3$ | t-Bu | $CH_3$ |
| 17 | $CH_3O$ | $CH_2OCOCH_3$ | t-Bu | Ph |
| 18 | $CH_3O$ | $CH_2OCOCH_3$ | t-Bu | 4-carboxyphenyl |
| 19 | $CH_3O$ | $CH_2S$-(1-methyltetrazol-5-yl) | t-Bu | Ph |
| 20 | $CH_3O$ | $CH_2S$-(4-methylthiadiazol-2-yl) | t-Bu | 4-carboxyphenyl |
| 21 | $CH_3O$ | $CH_2S$-(3-methyl-6-hydroxy-5-oxo-triazinyl) | t-Bu | $CH_3$ |

TABLE 1-continued
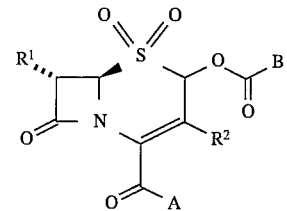
| n | R¹ | R² | A | B |
|---|---|---|---|---|
| 22 | " | " | " | Ph |
| 23 | CH₃O | CH₃ | Ph | CH₃ |
| 24 | " | " | " | Ph |
| 25 | " | " | " | 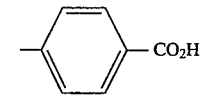 |
| 26 | " | CH₂OCOCH₃ | " | Ph |
| 27 | " | 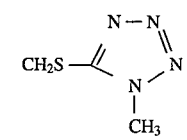 | " | Ph |
| 28 | CH₃O | 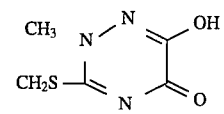 | Ph | Ph |
| 29 | CH₃O | CH₃ | 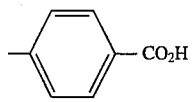 | Ph |
| 30 | CH₃O | CH₃ | 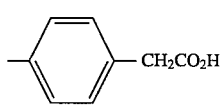 | Ph |
| 31 | CH₂—CH—CH₂ | CH₃ | t-Bu | Ph |
| 32 | " | " | " | 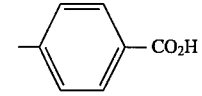 |
| 33 | " | " | Ph | Ph |
| 34 | " | " | " | " |
| 35 | CH₃CONH | " | " | " |
| 36 | CF₃CONH | " | " | " |
| 37 | HCONH | " | t-Bu | " |
| 38 | CH₃O | CH₃ | t-Bu | 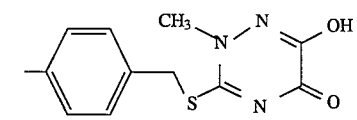 |
| 39 | " | " | Ph | " |
| 40 | " | " | t-Bu | 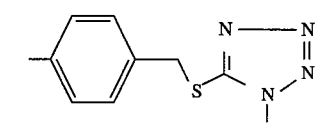 |
| 41 | " | " | Ph | " |

TABLE 1-continued

| n | R¹ | R² | A | B |
|---|---|---|---|---|
| 42 | " | " | t-Bu | 4-methylbenzyl-S-(1-CH₂COOH-tetrazol-5-yl) |
| 43 | " | " | Ph | " |
| 44 | " | " | t-Bu | 4-methylbenzyl-S-C(=N-N=C-CH₂COOH)-S |
| 45 | " | " | Ph | " |
| 46 | " | " | t-Bu | 4-methylbenzyl-S-C(=N-N=C-SCH₂COOH)-S |
| 47 | " | " | Ph | " |
| 48 | " | " | t-Bu | 4-methylbenzyl-SCH₂COOH |
| 49 | " | " | Ph | " |
| 50 | " | " | t-Bu | 4-methylbenzyl-OCH₂COOH |
| 51 | " | " | Ph | " |
| 52 | CH₃O | CH₃ | t-Bu | 4-methylphenyl-CONH-phenyl-4-CO₂H |
| 53 | " | " | Ph | " |
| 54 | " | " | t-Bu | 4-methylphenyl-CONHCH₂-phenyl-4-CO₂H |
| 55 | " | " | Ph | " |
| 56 | " | " | t-Bu | 4-methylphenyl-CONH-phenyl-4-CH₂CO₂H |
| 57 | " | " | Ph | " |
| 58 | " | " | t-Bu | 4-methylphenyl-CONH-phenyl-3-CO₂H |

TABLE 1-continued

| n | R¹ | R² | A | B |
|---|---|---|---|---|
| 59 | " | " | Ph | " |
| 60 | " | " | t-Bu | -C₆H₄-CH₂OCONH-C₆H₄-CO₂H |
| 61 | " | " | Ph | " |
| 62 | " | " | t-Bu | -C₆H₄-CH₂S-C₆H₄-CO₂H |
| 63 | " | " | Ph | " |
| 64 | " | " | t-Bu | -C₆H₄-CH₂O-C₆H₄-CO₂H |
| 65 | " | " | Ph | " |
| 66 | CH₃O | CH₃ | t-Bu | -C₆H₄-CH₂-S-CH₂CH(NH₂)CO₂H |
| 67 | " | " | Ph | " |
| 68 | " | " | t-Bu | -C₆H₄-CH₂-S-CH₂CH(NHCOCH₃)CO₂H |
| 69 | " | " | Ph | " |
| 70 | " | " | t-Bu | -C₆H₄-CH₂-S-CH₂CH(CO₂H)CO₂H |
| 71 | " | " | Ph | " |
| 72 | " | " | t-Bu | -C₆H₄-CH₂-S-CH₂-CO₂H |
| 73 | " | " | Ph | " |
| 74 | " | " | t-Bu | -C₆H₄-CH₂-S-CH₂CH₂-SO₃Na |
| 75 | " | " | Ph | " |

TABLE 1-continued

[Structure: β-lactam with R¹, sulfonyl group, R², A, and OC(O)B substituents]

| n | R¹ | R² | A | B |
|---|----|----|---|---|
| 76 | " | " | t-Bu | 4-(benzylthio-2-carboxyphenyl) substituted phenyl (–C₆H₄–CH₂S–C₆H₄–CO₂H) |
| 77 | " | " | Ph | " |
| 78 | " | " | t-Bu | 4-[(3-carboxypyridin-2-yl)thiomethyl]phenyl |
| 79 | " | " | Ph | " |
| 80 | CH₃O | CH₃ | t-Bu | H |
| 81 | " | " | t-Bu | 4-biphenyl |
| 82 | " | " | Ph | " |
| 83 | " | " | t-Bu | 4-benzoylphenyl |
| 84 | " | " | Ph | " |
| 85 | " | " | t-Bu | 4-tert-butylphenyl |
| 86 | " | " | Ph | " |
| 87 | " | CH₂OCOPh | t-Bu | Ph |
| 88 | " | " | Ph | " |
| 89 | " | CH₃ | Ph | 2-naphthyl |
| 90 | " | " | t-Bu | 4-(NHCOCH₃)phenyl |
| 91 | " | " | Ph | " |
| 92 | " | " | t-Bu | 4-(NHCONH₂)phenyl |
| 93 | " | " | Ph | " |
| 94 | CH₃O | CH₃ | t-Bu | C(CH₃)₃ |
| 95 | " | " | Ph | " |
| 96 | " | " | t-Bu | CH(C₂H₅)(CH₂)₃CH₃ |
| 97 | " | " | " | CH₂NHCOPh |

TABLE 1-continued

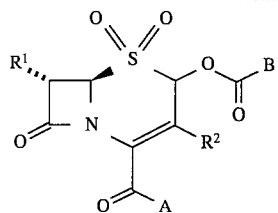

| n | $R^1$ | $R^2$ | A | B |
|---|---|---|---|---|
| 98 | " | " | " | $CH_2CH_2COPh$ |
| 99 | " | " | " | $-C_6H_5\text{-}4\text{-}SO_3H$ |
| 100 | " | " | Ph | " |
| 101 | " | " | " | $-C_6H_5\text{-}4\text{-}CH_2SO_3H$ |
| 102 | " | " | t-Bu | " |

The present invention also provides a process for the preparation of cephem sulphones of formula (I), which process comprises:

(i) reacting a compound of formula (II)

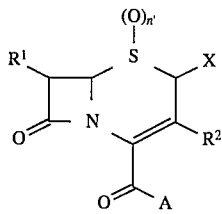

wherein either ($i_a$) n' is 0, 1 or 2; A, $R^1$ and $R^2$ are as defined above, and X is a leaving group, with a compound of formula (III)

B—C(O)O—M  (III)

wherein B is as defined above and M is hydrogen or a metal; or ($i_b$) n', A, $R^1$ and $R^2$ are as defined above, and X is hydrogen, with a compound of formula (IV)

B—C(O)O—O—W—B'  (IV)

wherein B is as defined above and B' being the same or different is as defined above for B and W is either a bond or a group selected from —C(O)—, —C(O)O—, —S(O)$_2$—, —C(O)NR$^v$— wherein R$^v$ is phenyl or a $C_1$-$C_4$ alkyl group;

(ii) if needed, when n in the compound of formula (I) is of higher value than n' in formula II as above defined, oxidizing the obtained compound to a compound of formula (I); and (iii) if desired, converting the resulting compound of formula (I) into a pharmaceutically or veterinarily acceptable salt thereof, and/or, if desired, converting the compound or salt into a stereoisomer, e.g. epimer, diastereoisomer, geometrical isomer or tautomer thereof.

In step ($i_a$) the leaving group X is typically a halogen, preferably bromine, chlorine or iodine. When M in formula (III) is hydrogen the acyloxylation reaction is usually performed in the presence of an inorganic or organic base. These external bases are generally not required when M of formula (III) is a metal, e.g an alkaline metal or a heavy metal, preferably a halophylic metal such as silver, copper, mercury or lead. The reaction ($i_a$) can be carried out in a wide range of organic solvents such as acetonitrile, N,N-dimethylformamide, dichloromethane, tetrahydrofuran, dioxane, ethyl acetate, chloroform, benzene, carbon tetrachloride, diethyl ether, dimethoxyethane, sulpholane, dimethylsulphoxide, hexamethylphosphoramide, N-methyl pyrrolidone, acetone, water and mixtures of any of these. Reaction temperatures range between –50° C. and +120° C., preferably between –20° C. and +80° C. Preferred external bases are tertiary organic bases either aliphatic or aromatic or alicyclic such as triethylamine, diisopropylethylamine, aniline, pyridine, lutidine, collidine, quinoline, N-methylmorpholine, N-methylpyrrolidine, diazabicyclooctane (DABCO); or inorganic bases such as alkaline bicarbonates, or carbonates, e.g. sodium bicarbonate, calcium carbonate, cesium carbonate, potassium carbonate. A beneficial effect has often been observed upon addition of alkaline metal salts such as sodium iodide or potassium iodide and additives such as molecular sieves, alumina or calcium oxide. The reaction can also be carried out in the presence of heavy metal salts such as silver nitrate, silver perchlorate, silver triflate, copper nitrate, mercury nitrate.

Step ($i_b$) is usually performed in the presence of tertiary aliphatic or aromatic organic bases such as 1,5-diazabicyclo [4,3,0]non-5-ene, 1,8-diazabicyclo[5,4,0]undec-7-ene, 1,1,3,3-tetramethylguanidine, 1,4-diazabicyclo [2,2,2]octane, N,N-diisopropylethylamine, N-methylmorpholine, N-methylpyrrolidine, triethylamine, pyridine, lutidine, collidine, quinoline. The reaction can be carried out in a wide range of non-protic organic solvents such as acetonitrile, N,N-dimethylformamide, tetrahydrofuran, dioxane, benzene, sulpholane, N,N-dimethylacetamide, hexamethylphosphoramide, N-methyl pyrrolidone or mixtures thereof. Temperatures for reaction ($i_b$) range between –60° C. and +40° C., preferably between –30° C. and room temperature.

If needed, the oxidation reaction mentioned in step (ii) is performed with organic or inorganic peracids or salts thereof, preferably peracetic acid, metachloroperbenzoic acid, permaleic acid, perphthalic acid, oxone, sodium or potassium persulphate in suitable organic solvents or mixtures of organic solvents with water. Preferred reaction temperatures range between –40° C. and +40° C.

It is understood that in the process above any functional group, if needed or desired can be masked by a conventional method and unmasked at the end or when convenient. It is also understood that the groups $R^1$, $R^2$, A and B can be converted by conventional methods into different groups included within those previously defined, if desired, at the end or at any stage of the process above. This conversion or masking/unmasking of the protecting groups are well known in the cephalosporin area (see, e.g. "Cephalosporins and Penicillins", E. H. Flynn Ed.).

Compounds of formula (II) are known or can be prepared from known compounds as described in EP-A-0337704. Compounds of formulae (III) and (IV) are known compounds or can be prepared from known compounds by known methods.

The potential of protease inhibitor therapy in the treatment of conditions resulting from the destruction of connective tissues has recently received particular attention. Much effort has been devoted to the search for inhibitors of human leucocyte elastase (HLE), which is the primary destructive agent in pulmonary emphysema and is probably involved in rheumatoid arthritis (J. C. Power, Am. Rev. Resp. Diseases 127, S54–S58, 1983; C. H. Hassal et al, FEBS Letters, 183, n. 2, 201, 1985, G. Weinbaum and V. V. Damiano, TIPS, 8, 6, 1987; M. Velvart, Rheumatol. Int. 1, 121, 1981). Low molecular weight inhibitors appear to have a number of advantages over natural high molecular weight protease inhibitors from either plant or animal sources: 1) they can be obtained in quantities; 2) they can be rationally designed or optimised; 3) they are not antigenic; and 4) they may be used orally or in aerosols. Many low molecular weight elastase inhibitors discovered so far contain reactive functional groups (chloromethyl ketones, isocyanates, etc); they may react with functional groups of proteins, and therefore they may be quite toxic. In this respect, β-lactam compounds are of potential interest because, though reactive towards serine protease, they are, as it is known, non-toxic at very high concentrations.

The compounds of the present invention are characterized by high inhibitory activity on elastases, especially human leucocyte elastase (HLE). In particular, the introduction of the acyloxy group O—C(O)—B, wherein B is as above described, at the C-2 position of the cephem nucleus, resulted in an unpredictable enhancement of inhibitory activity, relative to the corresponding C-2 unsubstituted compounds (formula (II)), which are disclosed in U.S. Pat. No. 5,077,286 (Dec. 31, 1991), while retaining good chemical stability.

When tested as inhibitors of human leucocyte elastase (HLE), compounds of formula (I) showed high "potency" (low value of apparent dissociation constant of HLE-inhibitors complex at steady rate $K_i^{SS}$) and high "efficiency" (high rate of formation of the HLE-inhibitor complex, $K_5/K_i$):

$$S + E \rightleftharpoons ES \rightarrow E + P$$
$$E + I \underset{k_4}{\overset{k_3}{\rightleftharpoons}} EI \overset{k_5}{\rightarrow} EI^* \overset{k_6}{\rightarrow} E + I^*$$

$$K_I = k_4/k_3 \qquad K_I^{SS} = K_I \frac{k_6}{(k_5 + k_6)}$$

wherein
E=enzyme (HLE)
S=substrate (see Protocol)
P=product (see Protocol)
I=inhibition
EI=Michaelis complex
EI*=covalent complex (inactivated enzyme)
I*=inactivated inhibitor To illustrate this point, Table 2 reports such parameters for a representative compound within the present invention (compound No.2 in Table 1), in comparison with the corresponding compound of formula (II) lacking the acyloxy group at the C-2 position. Table 2 incorporates, as a meaningful reference, the corresponding data obtained for L-659, 286, another β-lactam compound which was recently reported to undergo preclinical studies for the treatment and control of pulmonary emphysema (Am. Rev. Respir. Dis. 1988, 137, 204; Agents and Actions, 1988, 25, 60; Journal of Cellular Biochemistry 1989, 39, 47–53; J.Med. Chem. 1992, 35 3731–3744, compound 11f, in text and tables), which was independently synthesized in our laboratories. In addition, Table 3 reports the corresponding data for other compounds of the present invention, showing that excellent or superb potency is in general a common feature of this novel class of cephem derivatives. As a matter of fact, inhibition parameters were sometimes outside the determination limits of our experimental protocol ($K_i^{SS}$ less than 2 nanomolar, $K_5/K_I$ more than 2,000,000 $M^{-1}sec^{-1}$).

TABLE 2

Kinetic parameters for HLE-inhibition (see Protocol below) by a representative compound of the present invention (Compound No. 2 in Table I), the corresponding previous art compound, and a reference cephem sulphone selected as a particularly interesting HLE inhibitor (Merck S & D)

| Compound | Potency $K_i^{SS}$ (nM) | "Efficacy" $K_5/K_i (M^{-1}s^{-1})$ |
|---|---|---|
| Present invention[1] | <2 | $1.5 \times 10^6$ |
| Previous art[2] | 1300 | $0.6 \times 10^2$ |
| Reference | 75 | $9.2 \cdot 10^3$ |

1) Structure — FCE 28204 (Table 1, Compound No. 2)

TABLE 2-continued

2) Structure

FCE 25500
(Compd in U.S. Pat. No. 5,077,286, Example 2)

3) Structure

Merck S & D L-659,286
(see above for references)

TABLE 3

Kinetic parameters for HLE inhibitors (see Protocol below) by some representative compounds of the present invention

| Compound # | "Efficacy" $K_5/K_1$ (M$^{-1}$sec$^{-1}$) | "Potency" $K_i^{33}$ (nM) |
|---|---|---|
| 6 | 4 | 6.5 10$^4$ |
| 11 | <2* | >2* 10$^6$ |
| 19 | <2* | >2* 10$^6$ |
| 24 | 8 | ND |
| 25 | 29 | 3.4 10$^4$ |
| 38 | <2* | 7.0 10$^5$ |
| 80 | 600 | 1.4 10$^3$ |
| 83 | 2 | 5.0 10$^5$ |
| 87 | <2* | 1.6 10$^6$ |
| 94 | <2* | 1.5 10$^6$ |
| 96 | <2* | >2*10$^6$ |
| 98 | <2* | 3.0 10$^5$ |

(*) Values outside the determination limits allowed by the experimental protocol
ND: Not determined

Protocol

Kinetic parameters of HLE (Calbiochem) were determined at 37° C., 0.027M pH 7.4 phosphate buffer, 1% DMSO, 1% MeCN, NaCl (I=0.15), by monitoring the release of 7-amino-4-methylcoumarin (fluorescence detection) from N-methoxysuccinyl-alanyl-prolyl-valyl-7-amido-4-methylcoumarin as the substrate, according to the equations:

$$[P] = V_s t + \frac{V_z - V_s}{K}(1 - e^{kt})$$

$$K = K_6 + K_5 \frac{[I]/K_I}{1 + [S]/K_m + [I]/K_I}$$

$$V_s = V_o \frac{1 + [S]/K_m}{1 + [S]/K_m + [I]/K_i^{ss}}$$

wherein

[P], [I], [S]=product, inhibitor, and substrate concentration $V_s$=steady state rate $V_z$=zero time rate $V_o$=rate at [I]=0

$K_m$=Michaelis constant for the enzyme substrate pair (independently determined under the same experimental conditions). Full details of the Experimental Protocol are reported in M. Alpegiani et al., Eur. J. Med. Chem. 1992, 27, 875–890.

The compounds of formula (I) and their salts have high elastase-inhibiting activity and quite negligible toxicity (the orientative acute toxicity by i.v., oral or aerosol route is almost always greater than 500 mg/kg in rat). A patient is treated according to the present invention by a method comprising administering to the patient a therapeutically effective amount of a compound of formula (I) or a salt thereof. In this way the compounds and salts of the present invention can be used in the treatment of inflammatory and degenerative diseases caused by proteolytic enzymes in mammals including humans. For example, the compounds and their salts can be used to prevent or arrest the progression of diseases caused by proteolytic degradation of lungs and connective tissues, reduce inflammation and fever, and relieve pain. Such diseases are emphysema, acute respiratory distress syndrome, bronchial inflammation, rheumatoid arthritis, osteoarthritis, infectious arthritis, rheumatic fever, spondylitis, gout, lupus, psoriasis, and the like. The condition of the patient may thus be improved.

The present invention also provides a compound of formula (I), or a pharmaceutically or veterinarily acceptable salt thereof, for use as an elastase inhibitor. The invention further provides pharmaceutical and veterinary compositions containing a suitable carrier and/or diluent and, as an active principle, a 2-acyloxycephem sulphone of formula (I) or a pharmaceutically or veterinarily acceptable salt thereof. The pharmaceutical or veterinary compositions containing a compound of formula I or salt thereof may be prepared in a conventional way by employing conventional non-toxic pharmaceutical carriers or diluents in a variety of dosage forms and ways of administration.

The compounds of formula I can be administered:

A) Orally, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Formulation for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil. Aqueous suspensions contain the active materials in admixture with excipients suitable for the manufacture of aqueous suspensions. Such excipients are suspending agents, for example, sodium carboxymethylcellulose, methylcellulose, hydroxy propylmethylcellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl or n-propyl p-hydroxybenzoate, one or more colouring agents, one or more flavouring agents, or one or more sweetening agents, such as sucrose or saccharin. Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid. Dispersible powders and granules suitable for preparation or an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. Such formulations may also contain a demulcent, a preservative and flavouring and colouring agents.

B) Parenterally, either subcutaneously, or intravenously, or intramuscularly, or intrasternally, or by infusion techniques, in the form of sterile injectable aqueous or olagenous suspensions. The pharmaceutical compositions may be in the form of a sterile injectable aqueous or olagenous suspension.

This suspension may be formulated according to the known art using those suitable dispersing of wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium.

For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams ointments, jellies, solutions or suspensions.

The present invention further provides a method for controlling inflammatory and degenerative diseases by administering a therapeutically effective amount of one or more of the active compounds of formula I, or a pharmaceutically or veterinarily acceptable salt thereof, to humans or mammalians in need of such treatment.

Daily doses are in the range of about 0.1 to about 50 mg per kg of body weight, according to the activity of the specific compound, the age, weight and conditions of the subject to be treated, the type and severity of the disease, and the frequency and route of administration; preferably, daily dosage levels for humans are in the range of 20 mg to 2 g. The amount of active ingredient that may be combined with the carrier materials to produce a single dosage form will vary depending upon the host treated, for example his or her age, weight and condition, and the particular mode of administration. For example, a formulation intended for the oral administration to humans, may contain from 5 mg to 2 g of active agent compounded with an appropriate and convenient amount of carrier material which may vary from about 5 to about 95 percent of the total composition. Dosage unit forms will generally contain between from about 5 mg to about 500 mg of active ingredient.

The following examples further illustrate the invention.

EXAMPLE 1

2-Benzoyloxy-4-tert-butylcarbonyl-7α-methoxy-3-methyl-3-cephem 1,1-dioxide

Method A.

2-Bromo-4-tert-butylcarbonyl-7α-methoxy-3-methyl-3-cephem 1,1-dioxide (114 mg) was dissolved in dry acetonitrile (4 ml) and treated with silver benzoate (120 mg). After stirring for 30 minutes at room temperature, the reaction mixture was partitioned between EtOAc and water. Following drying over $Na_2SO_4$, the organic phase was rotoevaporated. The residue was passed through a silica gel column eluting with n-hexane/EtOAc mixtures. The title product was obtained as a white solid (85 mg).

NMR ($CDCl_3$, 200 MHz) 1.30 (9H,s); 1.76 (3H,s); 3.57 (3H,s); 4.88 (1H,d,J=1.8Hz); 5.20 (1H,d,J=1.8Hz); 5.92 (1H,s); 7.4–7.8 (5H,m). IR (KBr) 1795, 1755, 1700.

Method B.

1,5-Diazabicyclo[5,4,0]non-5-ene (0.13 ml) was added dropwise in 15 minutes to a mixture of 4-tert-butylcarbonyl-7α-methoxy-3-methyl-3-cephem 1,1-dioxide (301 mg) and benzoyl peroxide (242 mg) in dry acetonitrile (8 ml) under a nitrogen blanket while keeping the temperature at −5° C. After stirring for 20 minutes at 0° C., the reaction mixture was poured into EtOAc/water. The upper layer was dried ($Na_2SO_4$) and concentrated under vacuum. Flash chromatography of the residue allowed the isolation of unreacted starting material (120 mg) and gave the title product as a white powder (70 mg).

EXAMPLE 2

2-Acetoxy-4-tert-butylcarbonyl-7α-methoxy-3-methyl-3-cephem 1,1-dioxide (compound 6)

A mixture of 2-bromo-4-tert-butylcarbonyl-7α-methoxy-3-methyl-3-cephem 1,1-dioxide (100 mg) and silver acetate (50 mg) in acetonitrile (4 ml) was stirred at room temperature for 1 hour. After partitioning between EtOAc and water, the organic layer was dried ($Na_2SO_4$) then rotoevaporated. The residue was purified by flash chromatography (eluting with n-hexane/EtOAc mixtures) affording the title product as a waxy solid (76 mg).

NMR ($CDCl_3$, 200 MHz) 1.26 (9H,s); 1.68 (3H,s); 2.24 (3H,s); 3.54 (3H,s); 4.72 (1H,d,J=1.8Hz); 5.15 (1H,d,J=1.8Hz); 5.69 (1H,s).

EXAMPLE 3

Following the procedure described in Example 2 and using the suitable silver carboxylate the following products were obtained:

2-[4-(Benzoyl)benzoyloxy]-4-tert-butylcarbonyl-7α-methoxy-3-methyl-3-cephem 1,1-dioxide (compound 83)

NMR ($CDCl_3$, 200 MHz) 1.30 (9H,s); 1.77 (3H,s); 3.58 (3H,s); 4.87 (1H,d,J=8Hz); 5.21 (1H,d,J=1.8Hz), 5.94 (1H, s); 7.4–7.9 (5H,m); 7.90 (2H,d,J=8.4Hz); 8.19 (2h,d,J=8.4Hz) IR (KBr) 1800, 1750, 1705, 1760.

4-tert-Butylcarbonyl-7α-methoxy-3-methyl-2-[(β-naphthyl)oxy]-3-cephem 1,1-dioxide (compound 11)

NMR ($CDCl_3$, 200 MHz) 1.30 (9H,s); 1.79 (3H,s); 3.58 (3H, s); 4.93 (1H,d,J=1.7Hz); 5.22 (1H,d,J=1.7Hz); 5.97 (1H,s); 7.5–8.2 (7H,m) IR (KBr) 1790, 1740, 1700.

4-tert-Butylcarbonyl-2-formyl-7α-methoxy-3-methyl-3-cephem 1,1-dioxide (compound 80)

NMR ($CDCl_3$, 200 MHz) 1.28 (9H,s); 1.72 (3H,s); 3.56 (3H,s); 4.78 (1H,d,J=8Hz); 5.19 (1H,d,J=1.8Hz); 5.80 (1H, br.s); 8.23 (1H,d,J=0.9Hz) IR (KBr) 1795, 1755, 1700.

EXAMPLE 4

4-tert-Butylcarbonyl-2-{4-[(2,5-dihydro-6-hydroxy-2-methyl-5-oxo-1,2,4-triazin-3-yl)thiomethyl]benzoyloxy}-7α-methoxy-3-methyl-3-cephem 1,1-dioxide (compound 38)

A solution of 2-bromo-4-tert-butylcarbonyl-7α-methoxy-3-methyl-3-cephem 1,1-dioxide (110 mg) in acetonitrile (100 ml) was treated with 4-[(6-benzhydryloxy-2,5-dihydro-2-methyl-5-oxo-1,2,4- triazin-3-yl)thiomethyl]benzoic acid siver salt (230 mg). The reaction mixture was stirred at room temperature for 30 minutes, then diluted with EtOAC, filtered and rotoevaporated. Upon purification of the residue by flash chromatography 4-tert-butylcarbonyl-2-{4-[(6-benzhydryloxy-2,5-dihydro-2-methyl-5-oxo-1,2,4-triazin-3-yl)thiomethyl]benzoyloxy}-7α-methoxy-3-methyl-3-cephem 1,1-dioxide was obtained as a white solid (mg 75). This product was dissolved in methylene chloride (0.5 ml) and sequentially treated with anisole (0.03 ml) and trifluoroacetic acid (0.5 ml).

After stirring 30 minutes at room temperature, the solution was concentrated under vacuum. Addition of diisopropyl ether to the residue caused the formation of a whitish solid, which was filtered and dried in vacuo (40 mg) corresponding to the title product. IR (KBr) 1800, 1745, 1705.

EXAMPLE 5

2-Benzoyloxy-7α-methoxy-3-methyl-4-phenylcarbonyl-3-cephem 1,1-dioxide (compound 24)

A mixture of 2-bromo-7α-methoxy-3-methyl-4-phenylcarbonyl-3-cephem 1,1-dioxide ( 130 mg) and silver benzoate (115 mg) in acetonitrile (10 ml) was stirred at room temperature for 30 minutes. The reaction mixture was diluted with EtOAc, then filtered and the filtrate was rotoevaporated. The residue was purified by flash chromatography (eluting with n-hexane/EtOAc mixtures) affording the title product as a white powder (85 mg) IR (KBr) 1805, 1740, 1675.

NMR ($CDCl_3$, 200 MHz) 1.72 (3H,s); 3.55 (3H,s); 4.97 (1H,d,J=1.8Hz); 5.24 (1H,d,J=1.8Hz); 6.10 (1H,s); 7.4–8.2 (10H,m).

EXAMPLE 6

2-Benzoyloxy-3-benzoyloxymethyl-4-tert-butylcarbonyl-7α-methoxy-3-methyl-2(4-phenyl)benzoyloxy-3-cephem 1,1-dioxide (compound 87)

A mixture of 2-bromo-3-bromomethyl-4-tert-butylcarbonyl-7α-methoxy-3-cephem 1,1-dioxide (225 mg) and silver benzoate (350 mg) in acetonitrile (10 ml) was stirred at room temperature for 2 hours. After partitioning between EtOAc and water, the upper layer was dried (Na$_2$SO$_4$) and rotoevaporated. The residue was purified by flash chromatography (eluting with n-hexane/EtOAc mixtures) affording the title product as a white powder (90 mg) IR (KBr) 1800, 1755, 1740, 1700 (sh).

NMR (CDCl$_3$, 200 MHz) 1.36 (9H,s); 3.59 (3H,s); 4.73 (1H,d,J=13.5Hz); 4.80 (1H,d,J=13.5Hz); 4.99 (1H,d,J=2.1Hz); 5.13 (1H,d,J=2.1Hz); 6.26 (1H,s); 7.2–8.2 (10H,m).

EXAMPLE 7

4-tert-Butylcarbonyl-7α-methoxy-3-methyl-2-pivaloyloxy-3-cephem 1,1-dioxide (compound 94)

Starting from 2-bromo-4-tert-butylcarbonyl-7α-methoxy-3-methyl-3-cephem 1,1-dioxide and silver pivalate, and following the procedure described in Example 2, the title product was obtained as a white powder.

IR (KBr) $v_{max}$ 1795, 1765, 1705 cm$^{-1}$. NMR (CDCl$_3$) δ 1.27 (9H, s), 1.29 (9H, s), 1.67 (3H, s), 3.56 (3H, s), 4.70 (1H, d, J=1.8 Hz), 5.16 (1H, d, J=1.8 Hz), 5.67 (1H, s). FAB-MS 402 (MH$^+$).

EXAMPLE 8

4-Benzoyl-7α-methoxy-3-methyl-2-pivaloyloxy-3-cephem 1,1-dioxide (compound 95)

Starting from 4-benzoyl-2-bromo-7α-methoxy-3-methyl-3-cephem 1,1-dioxide and silver pivalate, and following the procedure described in Example 2, the title product was obtained as a white powder.

IR (KBr) $v_{max}$ 1790–1770, 1760, 1680 cm$^{-1}$. NMR (CDCl$_3$) δ 1.31 (9H, s), 1.63 (3H, s), 3.54 (3H, s), 4.79 (1H, d, J=1.9 Hz), 5.20 (1H, d, J=1.9 Hz), 5.85 (1H, s), 7.4–8.0 (sH, m). FAB-MS 422 (MH$^+$).

EXAMPLE 9

4-tert-Butylcarbonyl-2-(2-ethylhexanoyl)oxy-7α-methoxy-3-methyl-3-cephem 1,1-dioxide (compound 96)

Starting from 2-bromo-4-tert-butylcarbonyl-7α-methoxy-3-methyl-3-cephem 1,1-dioxide and silver 2-ethylhexanoate, and following the procedure described in Example 2, the title product was obtained as a white powder.

IR (CHCl$_3$) $v_{max}$ 1800, 1760, 1705 cm$^{-1}$.

EXAMPLE 10

4-tert-Butylcarbonyl-2-(2-ethylhexanoyl)oxy-7α-methoxy-3-methyl-3cephem 1,1-dioxide (compound 97)

Starting from 2-bromo-4-tert-butylcarbonyl-7α-methoxy-3-methyl-3-cephem 1,1-dioxide and hippuric acid silver salt, and following the procedure described in Example 2, the title product was obtained as a whitish foam.

IR (KBr) $v_{max}$ 1790, 1700, 1655 cm$^{-1}$. NMR (CDCl$_3$) δ1.27 (9H, s), 1.75 (3H, s), 3.55 (3H, s), 4.29 (1H, dd, J=4.9 and 18.3 Hz), 4.52 (1H, dd, J=6.1 and 18.3 Hz), 4.76 d, J=1.5 Hz), 5.18 (1H, d, J=1.5 Hz), 5.76 (1H, s), 6.76 (1H, m, exch. D$_2$O), 7.4–8.0 (5H, m).

EXAMPLE 11

2-[3-(Benzoyl)propionyl]oxy-4-tert-butylcarbonyl-7α-methoxy-3-methyl-3-cephem 1,1-dioxide.

(compound 98)

Starting from 2-bromo-4-tert-butylcarbonyl-7α-methoxy-3-methyl-3-cephem 1,1-dioxide and 3-(benzoyl)propionic acid silver salt, and following the procedure described in Example 2, the title product was obtained as a white powder.

IR (KBr) $v_{max}$ 1775, 1705, 1690 cm$^{-1}$. NMR (CDCl$_3$) δ 1.25 (9H, s), 1.78 (3H, s), 2.9–3.0 (2H, m), 3.3–3.5 (2H, m), 3.55 (3H, s), 4.76 (1H, d, J=1.5 Hz), 5.17 (1H, d, J=1.5 Hz), 5.70 (1H, s), 7.4–8.1 (5H, m).

EXAMPLE 12

2-Benzoyloxy-4-tert-butylcarbonyl-7α-methoxy-3-(1-methyl-1,2,3,4-tetrazol-5-yl)thiomethyl-3-cephem 1,1-dioxide (compound 19)

To a solution of 4-tert-butylcarbonyl-7α-methoxy-3-(1-methyl-1,2,3,4-tetrazol-5-yl)thiomethyl-3-cephem 1,1 dioxide (350 mg) in dichloromethane (30 ml), N-bromosuccinimide (200 mg) and triethylamine (0.13 ml) were added sequentially. The mixture was stirred for 15 min at room temperature. Following dilution with dichloromethane, the organic phase was sequentially washed with 4% aqueous NaHSO$_3$, saturated NaHCO$_3$ and water. After drying over Na$_2$SO$_4$ and removal of the solvent, the residue was purified by flash chromatography (eluting with hexane-EtOAc mixtures) affording 2-bromo-4-tert-butylcarbonyl-7α-methoxy-3-(1-methyl-1,2,3,4-tetrazol-5-yl) thiomethyl-3-cephem 1,1-dioxide as a waxy solid (200 mg), IR (KBr) $v_{max}$ 1800, 1700 cm$^{-1}$. A portion of this material (180 mg) was dissolved in acetonitrile (10 ml) and treated with silver benzoate (95 mg). The mixture was stirred for 30 min at room temperature, then filtered and rotoevaporated. Following flash chromatography (eluting with gradient of EtOAc in hexane) the title product was obtained as a light yellow solid (80 mg).

IR (KBr) $v_{max}$ 1805, 1750, 1700 cm$^{-1}$. NMR (CDCl$_3$) δ1.35 (9H, s), 3.59 (3H, s), 3.84 (3H, s), 3.87 and 4.19 (2H, each d, J=14.2 Hz), 4.99 (1H, d, J=1.9 Hz), 5.24 (1H, d, J=1.9 Hz), 6.25 (1H, s), 7.3–8.1 (5H, m).

EXAMPLE 13

4-tert-Butylcarbonyl-2-(4-carboxybenzoyl)oxy-7α-methoxy-3-methyl-3-cephem 1,1-dioxide (compound 3)

A solution of 2-bromo-4-tert-butylcarbonyl-7α-methoxy-3-methyl-3-cephem 1,1-dioxide (110 mg) in acetonitrile (200 mg) was treated with 4-(p-methoxybenzyloxycarbonyl)benzoic acid silver salt (200 mg). The resulting mixture was stirred for 5 hours at room temperature, then diluted with EtOAc, filtered, and sequentially washed with water, aqueous NaHCO$_3$ and brine. After drying over Na$_2$SO$_4$, the organic layer was concentrated to dryness. The oily residue was dissolved in dichloromethane (3 ml) and treated with anisole (0.1 ml) and trifluoroacetic acid (1 ml). After standing for 2 hours at r.t., the solvent was removed under reduced pressure and the residue was chromatographed over silica gel (eluting with gradient of EtOAc in hexane). The title product was obtained as a white solid (55 mg).

IR (KBr) $v_{max}$ 3500–2500, 1805, 1745, 1705 cm$^{-1}$. NMR (CDCl$_3$) δ1.31 (9H, s), 1.77 (3H, s), 3.58 (3H, s), 4.86 (1H, d, J=1.5 Hz), 5.21 (1H, d, J=1.5 Hz), 5.93 (1H, s), 8.0–8.2 (4H, m).

EXAMPLE 14

4-Benzoyl-2-(4-carboxybenzoyl)oxy-7α-methoxy-3-methyl-3-cephem 1,1-dioxide (compound 25)

Starting from 4-benzoyl-2-bromo-7α-methoxy-3-methyl-3-cephem 1,1-dioxide (110 mg) and 4-(p-methoxybenzyloxycarbonyl)benzoic acid silver salt (200 mg), and following the procedure described in Example 13, the title product was obtained as a white powder.

IR (KBr) $v_{max}$ 3500–2500, 1805, 1740, 1680 cm$^{-1}$. NMR (CDCl$_3$) δ1.72 (3H, s), 3.55 (3H, s), 4.96 (1H, d, J=1.7 Hz), 5.25 (1H, d, J=1.5 Hz), 6.11 (1H, s), 7.4–8.4 (9H, m).

EXAMPLE 15

4-Benzoyl-2-benzoyloxy-3-benzoyloxymethyl-7α-methoxy-3-cephem 1,1-dioxide (compound 88)

Starting from 4-benzoyl-2-bromo-3-bromomethyl-7α-methoxy-3cephem 1,1-dioxide and silver benzoate, and following the procedure described in Example 6 the title product was obtained as a white powder.

IR (KBr) $v_{max}$ 1810, 1745, 1680 cm$^{-1}$. NMR (CDCl$_3$) δ3.56 (3H, s) , 3.81 (1H, d, J=11.9 Hz), 3.93 (1H, d, J=11.9 Hz), 5.10 (1H, d, J=1.6 Hz), 5.22 (1H, d, J=1.6 Hz), 6.53 (1H, s), 7.4–8.2 (15H, m).

GENERAL PROCEDURE FOR PREPARING SILVER CARBOXYLATES

A mixture of the proper carboxylic acid (10 mmol) in water (50 mL) was treated with sodium methoxide (0.54 g, 10 mmol) and stirred until a clear solution appeared. Silver nitrate (1.7 g, 10 mmol) was then added in the dark, causing the immediate formation of a white precipitate. After stirring for few minutes, the mixture was filtered and the solid was sequentially washed with water and ethyl ether. Following drying in an oven at 55° C. under vacuum, silver carboxylates were obtained as whitish or light grey powders in yields ranging from 60% to 95%.

We claim:

1. A compound of the formula (I), or a pharmaceutically or veterinarily acceptable salt thereof;

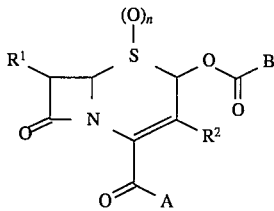

(I)

wherein n is one or two;

A and B are each, independently, hydrogen or an organic radical selected from optionally substituted $C_1$–$C_{12}$ straight or branched alkyl, $C_2$–$C_{12}$ alkenyl, $C_2$–$C_{12}$ alkynyl, $C_6$–$C_{14}$ aryl, $C_3$–$C_8$ cycloalkyl, $C_5$–$C_8$ cycloalkenyl, or $C_7$–$C_{18}$ aralkyl, $C_8$–$C_{18}$ aralkenyl, $C_8$–$C_{18}$ aralkynyl, ($C_{3–8}$cycloalkyl) alkyl, ($C_{3–8}$cycloalkyl) alkenyl, heterocyclyl, (heterocyclyl) alkyl and (heterocyclyl)alkenyl groups, wherein a heterocyclyl group is a 3- to 6-membered, saturated or unsaturated heterocyclyl ring containing at least one hetero atom selected from the group consisting of O, S and N, which is optionally fused to a second 5- or 6-membered, saturated or unsaturated heterocyclyl group, to a cycloalkyl group or to an aryl group;

$R^1$ represents (1) a chlorine, fluorine, bromine or iodine atom;

(2) A as defined above;

(3) an ether OA wherein A is as defined above;

(4) a thioether, sulphoxide or sulphone —S(O)$_m$A wherein m is either zero, one or two and A is as defined above;

(5) acyloxy —OC(O)A wherein A is as defined above;

(6) sulfonyloxy —OS(O)$_2$A wherein A is as defined above;

(7) an acylamino group —NHC(O)A wherein A is as defined above or acylamino —NH—Z wherein Z is a mono, di- or tripeptide composed of D or L α-aminoacids selected from the group consisting of Ala, Gly, Val, Leu, Ile and Phe and with the terminal amino group either free or acylated by a group —C(O)A or —C(O)OA wherein A is as defined above;

$R^2$ represents (1) A as defined above;

(2) a chlorine or fluorine atom;

(3) a sulphenyl, sulfinyl or sulfonyl group —S(O)$_m$A wherein A is as defined above;

(4) an oxy group —O—A wherein A is as defined above;

(5) an acyl group —C(O)A or acyloxy group —C(O)OA wherein A is as defined above;

(6) on oxymethyl group —CH$_2$—OA wherein A is as defined above;

(7) a thiomethyl group or a derivative thereof of formula —CH$_2$S(O)$_m$A wherein m and A are as defined above;

(8) an acyloxymethyl group —CH$_2$OC(O)A or —CH$_2$O—Z wherein A and Z are as defined above;

(9) an acylthiomethyl group —CH$_2$SC(O)A wherein A is as defined above;

(10) an aminomethyl group —CH$_2$—N(A)A' wherein A is as defined above and A', being the same or different, is as defined above for A; or A and A' taken together with the nitrogen atom to which they are attached represent a heterocyclic ring;

(11) ammoniomethyl —CH$_2$N$^+$(A)(A')A" wherein A and A' are as defined above and A", being the same or different, is as defined for A; or A is alkyl and A' and A" together with the nitrogen atom to which they are attached represent a heterocyclic ring, or A and A' and A" together with the nitrogen atom to which they are attached represent a heterocyclic ring, wherein a heterocyclic ring is of the same cyclic structure defined above for a heterocyclyl group;

(12) an acylaminomethyl group —CH$_2$NH—C(O)A or —CH$_2$NH—Z wherein A and Z are as defined above.

2. A compound according to claim 1 having the configuration of formula (I'):

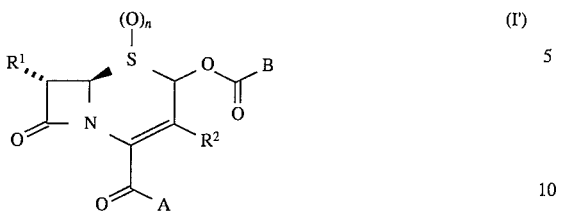

wherein n is one or two;

A is hydrogen or $C_1$–$C_{12}$ straight or branched alkyl, $C_2$–$C_{12}$ alkenyl, $C_2$–$C_{12}$ alkynyl, $C_6$–$C_{10}$ aryl, $C_3$–$C_8$ cycloalkyl, heterocyclyl, 2-phenyl-2-propyl, benzyl or diphenylmethyl, wherein the alkyl, alkenyl, alkynyl, aryl, cycloalkyl, heterocyclyl and benzyl groups are either unsubstituted or substituted by fluoro, chloro, sulfo, carboxy, $C_1$–$C_4$ alkoxy, $C_1$–$C_4$ alkoxycarbonyl, carbamoyl, sulfamoyl, carbamoyloxy, methanesulphonyl, nitro, cyano, diazo, hydroxy, methoxy, ethoxy, tert-butoxy, benzyloxy, benzhydryloxy, acetoxy, pivaloyloxy, benzoxy, carboxymethyl, carboxyphenyl $C_6H_5$—COOH, carboxybenzyl, $CH_2$—$C_6H_4$—COOH benzoyl, pivaloyl, amino, formamido, acetamido, trifluoroacetamido or pivalamido;

B is
(1') a hydrogen atom;
(2') an optionally substituted $C_{1-C5}$ straight or branched alkyl or alkenyl group, or $C_3$–$C_6$ cycloalkyl;
(3') optionally substituted $C_6$–$C_{14}$ aryl;
(4') optionally substituted $C_7$–$C_{14}$ aralkyl;
(5') optionally substituted heterocyclyl;
(6') optionally substituted (heterocyclyl)alkyl; the substituents for the groups defined under (1')–(6') being selected from the group consisting of fluoro, chloro, bromo, nitro, cyano, sulfo, carboxy, tetrazolyl, $C_1$–$C_4$ alkoxycarbonyl, carbamoyl, N-carboxyphenylcarbamoyl, N-carboxybenzylcarbamoyl, N-carboxymethylphenylcarbamoyl, sulfamoyl, carbamoyloxy, methanesulfonyl, hydroxy, $C_1$–$C_4$ alkoxy, benzyloxy, benzhydryloxy, phenoxy, p-chlorophenoxy, p-carboxyphenoxy, acetoxy, pivaloyloxy, benzoyloxy, methylthio, phenylthio, methanesulfonyl, benzenesulfonyl, carboxymethylthio, carboxyphenyl $C_6H_5$—COOH, carboxybenzyl $CH_2$—$C_6H_4$—COOH, acetyl, trifluoroacetyl, benzoyl, pivaloyl, amino, dimethylamino, phenylamino, 2,6-dichlorophenylamino, diethylamino, formamido, acetamido, trifluoroacetamido, pivalamido, oxo, phenyl, phthalimido, isoindolinyl, 1-oxoisoindolinyl and $C_1$–$C_5$ straight or branched alkyl, vinyl or allyl, and $C_1$–$C_4$ alkyl substituted by one or more substituents selected from the group consisting of chloro, fluoro, difluoro, trifluoro, amino, N,N dimethylamino, azido, cyano, carboxy, sulfo, carbamoyl, carbamoyloxy, hydroxy, $C_1$–$C_4$ alkyloxycarbonyl, guanidino and a group Y—A''', wherein Y is oxygen, sulphur or carbamoyl(oxy) and A''' is an optionally substituted $C_1$–$C_4$ alkyl, phenyl, benzyl or heterocyclic group, the optional substituents being selected from those defined above for groups (1')–(5');

$R^1$ is
(1') hydrogen or chlorine, fluorine or bromine atom;
(2') $C_1$–$C_4$ alkyl, $C_1$–$C_4$ alkenyl, 1-(hydroxy)ethyl, 1-(benzyloxy)ethyl, 1-(benzyloxycarbonyloxy)ethyl, 1-(phenylacetoxy)ethyl, 2-fluoro-1-hydroxyethyl, phenyl or benzyl;

(3') methoxy, ethoxy, isopropoxy, phenoxy or benzyloxy;
(4') methylthio, ethylthio, isopropylthio;
(5') formyloxy, acetoxy or phenylacetoxy;
(6') mesyloxy or tosyloxy;
(7') formamido, acetamido, fluoroacetamido, trifluoroacetamido or chloroacetamido;
(8') $R^{iv}$-Ala-NH, wherein $R^{iv}$ is acetyl, tert-butoxycarbonyl, benzoxycarbonyl or HOOC—$CH_2CH_2C(O)$—;
(9') $R^{iv}$-Val-NH, wherein $R^{iv}$ is as defined above;
(10') Val-Pro-NH, LysNH or Ala-Ala-ProNH, wherein the terminal amino group of Val, Lys or Ala respectively or the α-amino group of Lys is either free or acylated with a group $R^{iv}$ as defined above;

$R^2$ is either hydrogen or
(1') methyl, chloromethyl, bromomethyl, benzyl, ethyl, propyl or phenyl;
(2') chloro;
(3') methoxy or benzyloxy;
(4') methylthio;
(5') formyl, acetyl, benzoyl, carboxy, methoxycarbonyl, ethoxycarbonyl, tert-butoxycarbonyl or benzyloxycarbonyl;
(6') methoxymethyl, ethoxymethyl, isopropoxymethyl; or benzyloxymethyl, phenoxymethyl, 3-pyridyloxymethyl wherein the phenyl and pyridyl rings are either unsubstituted or substituted by one group or two groups which are the same or different and are each selected from the group consisting of hydroxy, carboxy, amino and $C_1$–$C_4$ alkoxycarbonyl;
(7') —$CH_2(S)_n$A wherein n is zero, one or two and A is as defined above or as defined in claim 1;
(8') acetoxymethyl, benzoyloxymethyl, phenylacetoxymethyl or $C_3$–$C_6$ alkanoyloxymethyl, which groups are either unsubstituted or substituted by one or more groups selected from the group consisting of carboxy, hydroxy and $C_1$–$C_3$ alkoxy;
(9') trialkylammoniomethyl wherein the alkyl group is methyl, ethyl or propyl; N-methylpyrrolidiniomethyl, N-methylpiperidiniomethyl or N-methylmorpholiniomethyl;
(10') pyridiniomethyl which is either unsubstituted or substituted on the heterocyclic ring by fluoro, chloro, methoxy, hydroxy, carboxy or carbamoyl;
(11') carbamoyloxymethyl; or
(12') carboxy;
or a pharmaceutically or veterinarily acceptable salt thereof, or a stereoisomer, epimer, diastereoisomer, geometrical isomer, or tautomer thereof, wherein the terms "heterocyclyl", "heterocyclic group" and "heterocyclic ring" are heterocyclic systems of 3- to 6-membered, saturated or unsaturated heterocyclyl rings containing at least one hetero atom selected from O, S and N, which is optionally fused to a second 5- or 6-membered, saturated or unsaturated heterocyclyl group, to a cycloalkyl group or to an aryl group.

3. A process for preparing a compound of the formula (I) as defined in claim 1 or a pharmaceutically or veterinarily acceptable salt thereof, which process comprises:

(i) reacting a compound of formula (II)

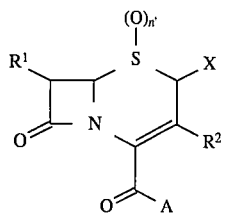

wherein either ($i_a$) n' is 0, 1 or 2; A, $R^1$ and $R^2$ are as defined in claim 1, and X is a leaving group, with a compound of formula (III)

wherein B is as defined in claim 1 and M is hydrogen or a metal; or ($i_b$) n' A $R^1$ and $R^2$ are as defined above and X is hydrogen, with a compound of formula (IV)

wherein B is as defined above and B', being the same or different is as defined above for B, and W is either a bond or a group selected from —C(O)—, —C(O)O—, —S(O)$_2$— and —C(O)NR$^v$— wherein R$^v$ is phenyl or a $C_1$–$C_4$ alkyl group;

(ii) if needed, when n in the compound of formula (I) is of higher value than n' in formula (II) as above defined, oxidizing the obtained compound to a compound of formula (I); and (iii) if desired, converting the resulting compound of formula (I) into a pharmaceutically or veterinarily acceptable salt thereof and/or, if desired, converting the compound or salt thereof into a stereoisomer, epimer, diastereoisomer, geometrical isomer or tautomer thereof.

4. A process according to claim 3 in which X is bromine, chlorine or iodine, M is hydrogen and the reaction ($i_a$) is performed in the presence of an inorganic or organic base, optionally in the presence of sodium iodide or potassium iodide, molecular sieves, alumina or calcium oxide, or of silver nitrate, silver perchlorate, silver triflate, copper nitrate or mercury nitrate.

5. A process according to claim 3 or 4 in which the reaction ($i_a$) is performed in the presence of an organic base selected from triethylamine, diisopropylethylamine, aniline, pyridine, lutidine, collidine, quinoline, N-methylmorpholine, N-methylpyrrolidine and diazabicyclooctane (DABCO); or an inorganic base selected from sodium bicarbonate, calcium carbonate, cesium carbonate and potassium carbonate.

6. A process according to claim 3, in which x is bromine, chlorine or iodine and M is silver, copper, mercury or lead.

7. A process according to claim 3 in which the reaction ($i_a$) is carried out in acetonitrile, N,N-dimethylformamide, dichloromethane, tetrahydrofuran, dioxane, ethyl acetate, chloroform, benzene, carbon tetrachloride, diethyl ether, dimethoxyethane, sulpholane, dimethylsulphoxide, hexamethylphosphoramide, N-methyl pyrrolidone, acetone, water or a mixture of any of these at a temperature of from −50° C. to +120° C.

8. A process according to claim 3 in which the reaction ($i_b$) is performed in the presence of 1,5-diazabicyclo[4,3,0] non-5-ene, 1,8-diazabicyclo [5,4,0]undec-7-ene, 1,1,3,3-tetra methylguanidine, 1,4-diazabicyclo[2,2,2] octane, N,N-diiso propylethylamine, N-methylmorpholine, N-methylpyrrolidine, triethylamine, pyridine, lutidine, collidine or quinoline, in acetonitrile, N,N-dimethylformamide, tetrahydrofuran, dioxane, benzene, sulpholane, N,N-dimethylacetamide, hexamethyl phosphoramide, N-methyl pyrrolidone, or a mixture of any of these, at a temperature of −60° C. to +40° C.

9. A compound of formula (I) or a pharmaceutically or veterinarily acceptable salt thereof, as claimed in claim 1 or 2, for use in a method of treatment of the human or animal body by therapy.

10. A compound or salt according to claim 9 for use as an elastase inhibitor.

11. A pharmaceutical or veterinary composition comprising a carrier and/or diluent and, as an active principle, a compound as claimed in claim 1 or 2 or a pharmaceutically or veterinarily acceptable salt thereof.

12. The compound of claim 1, wherein, for radical A or B, said straight or branched alkyl is methyl, ethyl, n-propyl, isopropyl, n-butyl, isobutyl, sec-butyl, tert-butyl, n-pentyl, or n-hexyl; said alkenyl group is vinyl, allyl, crotyl, 2-methyl-1-propenyl, 1-methyl-1-propenyl, butenyl or pentenyl; said alkynyl is ethynyl, propargyl, 1-propynyl, 1-butynyl or 2-butynyl; said aryl is phenyl, naphthyl, phenanthryl or anthryl; said cycloalkyl is cyclopropyl, cyclobutyl, cyclopentyl or cyclohexyl; said cycloalkenyl is cyclopentenyl or cyclohexenyl; said aralkyl is benzyl, phenylethyl, naphthylmethyl, naphthylethyl or anthrylmethyl; said aralkenyl is styryl, 2-phenyl-1-propenyl, 3-phenyl-2-butenyl, 2-naphthylethenyl or anthrylethenyl; said aralkynyl is 2-phenylethynyl, 2-napthylethynyl or anthrylethynyl; said (cycloalkyl)alkyl is a cycloalkyl group linked to a $C_{1-4}$ alkyl group; said cycloalkylalkenyl is a cycloalkyl group linked to a $C_{2-4}$ alkenyl group; said (heterocyclyl)alkyl group is a heterocyclyl group linked to a $C_{1-4}$ alkyl group and said (heterocyclyl)alkenyl group is a heterocyclic group linked to a $C_{2-4}$ alkenyl group.

* * * * *